United States Patent [19]
Claremon et al.

[11] Patent Number: 5,700,797
[45] Date of Patent: Dec. 23, 1997

[54] N-(2,4-DIOXO-2,3,4,5-TETRAHYDRO-1H-1,5-BENZODIAZEPIN-3-YL)-3-AMIDES

[75] Inventors: David A. Claremon, Maple Glen; Nigel Liverton, Harleysville; Harold G. Selnick, Ambler, all of Pa.

[73] Assignee: Merck & Co., Inc., Rahway, N.J.

[21] Appl. No.: 476,301

[22] Filed: Jun. 7, 1995

[51] Int. Cl.⁶ ............. C07D 243/12; A61K 31/55
[52] U.S. Cl. ............................... 514/221; 540/518
[58] Field of Search ............... 540/518; 514/221

[56] References Cited

U.S. PATENT DOCUMENTS

| | | | |
|---|---|---|---|
| 4,470,988 | 9/1984 | Watthey | 424/263 |
| 4,473,575 | 9/1984 | Watthey | 424/263 |
| 4,503,060 | 3/1985 | Walther et al. | 514/214 |
| 4,507,313 | 3/1985 | Braestrap et al. | 514/220 |
| 4,537,885 | 8/1985 | Watthey | 514/183 |
| 4,600,534 | 7/1986 | Bach et al. | 260/239.3 B |
| 4,692,522 | 9/1987 | Parsons et al. | 540/523 |
| 4,775,671 | 10/1988 | Hunkeler et al. | 514/220 |
| 4,820,834 | 4/1989 | Evans et al. | 540/504 |
| 4,847,248 | 7/1989 | Freidinger et al. | 514/214 |
| 4,992,437 | 2/1991 | Naka et al. | 514/220 |
| 5,004,741 | 4/1991 | Evans et al. | 514/221 |
| 5,055,464 | 10/1991 | Murakami et al. | 514/211 |
| 5,166,151 | 11/1992 | Freidinger et al. | 514/215 |
| 5,206,234 | 4/1993 | Bock et al. | 514/213 |
| 5,220,018 | 6/1993 | Bock et al. | 514/221 |
| 5,302,591 | 4/1994 | Fletcher et al. | 514/221 |
| 5,324,726 | 6/1994 | Bock et al. | 514/221 |
| 5,338,861 | 8/1994 | Botta et al. | 548/552 |
| 5,360,802 | 11/1994 | Chambers et al. | 514/221 |
| 5,410,049 | 4/1995 | Chambers | 514/504 |
| 5,426,185 | 6/1995 | Baldwin et al. | 540/509 |
| 5,428,157 | 6/1995 | Baldwin et al. | 540/509 |
| 5,438,055 | 8/1995 | Baldwin et al. | 514/221 |
| 5,439,905 | 8/1995 | Naka et al. | 514/220 |
| 5,439,906 | 8/1995 | Bock et al. | 514/220 |
| 5,504,077 | 4/1996 | Collins et al. | 514/211 |

FOREIGN PATENT DOCUMENTS

| | | |
|---|---|---|
| 1 190 708 | 7/1985 | Canada . |
| 0 107 095 A1 | 5/1984 | European Pat. Off. . |
| 0 514 133 A1 | 11/1992 | European Pat. Off. . |
| 0 538 945 A1 | 4/1993 | European Pat. Off. . |
| 0 566 175 A2 | 10/1993 | European Pat. Off. . |
| WO 93/02078 | 2/1993 | WIPO . |
| WO 93/08176 | 4/1993 | WIPO . |
| WO 93/07131 | 4/1993 | WIPO . |
| WO 93/15068 | 8/1993 | WIPO . |
| WO 93/19063 | 9/1993 | WIPO . |
| WO 93/17011 | 9/1993 | WIPO . |
| WO 94/05673 | 3/1994 | WIPO . |

OTHER PUBLICATIONS

Trist et al, Chemical Abstracts vol. 120, entry 164241 (1994).

Finch et al., Chemical Abstracts, vol. 120, entry 134541 (1994).

Gasc et al., Chemical Abstracts, vol. 114, entry 62127 (1991).

J. Gen. Physiol., vol. 96, pp. 195–215 (Jul. 1990), by M.C. Sanguinetti, et al.

J. Cardiovasc. Pharmacol., vol. 20, (Suppl. 2) pp. S17–S22 (1992), by L. M. Hondeghem.

*Primary Examiner*—John M. Ford
*Attorney, Agent, or Firm*—Elliott Korsen; Frances P. Bigley; Mark R. Daniel

[57] ABSTRACT

This invention is concerned with novel compounds represented by structural formula I

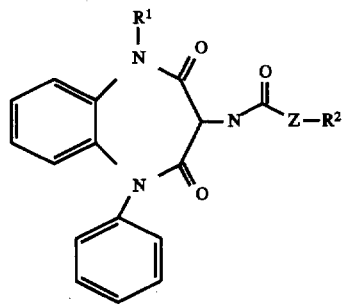

FORMULA I which are useful in the treatment of arrhythmia.

5 Claims, No Drawings

N-(2,4-DIOXO-2,3,4,5-TETRAHYDRO-1H-1,5-BENZODIAZEPIN-3-YL)-3-AMIDES

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, agents which exhibit both satisfactory effects and high safety profiles have not been marketed. For example, antiarrythmic agents of Class I, according to the classification of Vaughan-Williams, which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect in that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

SUMMARY OF THE INVENTION

This invention is concerned with novel compounds represented by structural formula I

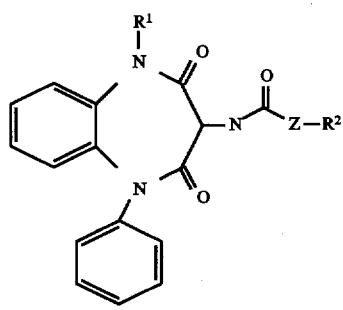

FORMULA I where
R$^1$ is C$_{1-6}$ alkyl, either straight or branch chain; substituted C$_{1-6}$alkyl, either straight or branch chain wherein the substitutents are selected from F, C$_{3-8}$ cycloalkane, —OH, —CF$_3$, Z is
1) C$_{1-6}$ alkyl, either straight or branch chain,
2) substituted C$_{1-6}$ alkyl, either straight or branch chain, wherein the substitutents are selected from F, OH, NO$_2$,
3) C$_{2-4}$ alkenylene, either straight or branch chain,
4) —(CH$_2$)$_m$—W—(CH$_2$)$_n$— wherein m and n are independently 0, 1, 2, 3 or 4 and W is —O—, —S— or —NH,
5) C$_{3-6}$ cycloalkane,
6) C$_{3-6}$ cycloalkylene, or
7) single bond;

R$^2$ is
1) phenyl, either unsubstituted or substituted with one or two substituents selected from
   a) —NO$_2$, —OH,
   b) —Cl, Br, F, or I,
   c) —CF$_3$,
   d) —C$_{1-3}$ alkyl,
   e) —C$_{1-3}$ alkoxy,
   f) —CN,
   g) -methylenedioxy,
2) C$_{5-7}$ cycloalkyl, either unsubstituted or substituted with one or two substitutents selected from
   a) —NO$_2$, —OH,
   b) —F,
   c) —CF$_3$,
   d) —C$_{1-3}$ alkyl,
   e) —C$_{1-3}$ alkoxy,
   f) —CN,
   g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment.

DETAILED DESCRIPTION OF THE INVENTION

The novel compounds of this invention have structural formulae

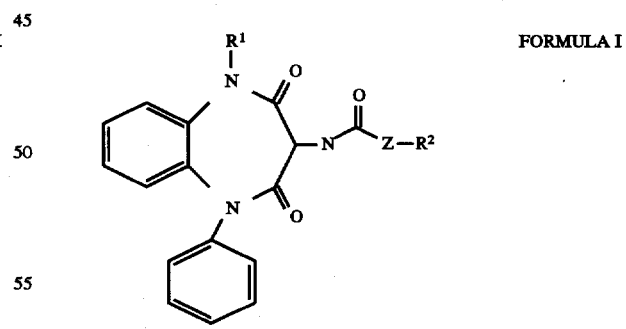

FORMULA I where
R$^1$ is C$_{1-6}$ alkyl, either straight or branched chain; substituted C$_{1-6}$alkyl, either straight or branched chain wherein the substitutents are selected from F, C$_{3-8}$ cycloalkane, —OH, —CF$_3$, and Z is
1) C$_{1-6}$ alkyl, either straight or branch chain,
2) substituted C$_{1-6}$ alkyl, either straight or branched chain, wherein the substitutents are selected from F, OH, NO$_2$, 2) $C_{2-4}$ alkenylene, either straight or branch chain,
3) —$(CH_2)_m$—W—$(CH_2)_n$— wherein m and n are independently 0, 1, 2, 3 or 4 and W is —O—, —S— or —NH,
4) $C_{3-6}$ cycloalkane,
5) $C_{3-6}$ cycloalkylene, or
6) single bond;

$R^2$ is
1) phenyl, either unsubstituted or substituted with one or two substituents selected from
   a) —$NO_2$, —OH
   b) —Cl, Br, F, or I,
   c) —$CF_3$,
   d) —$C_{1-3}$ alkyl,
   e) —$C_{1-3}$ alkoxy,
   f) —CN,
   g) -methylenedioxy,
2) $C_{5-7}$ cycloalkyl, either unsubstituted or substituted with one or two substitutents selected from
   a) —$NO_2$, —OH
   b) —F,
   c) —$CF_3$,
   d) —$C_{1-3}$ alkyl,
   e) —$C_{1-3}$ alkoxy,
   f) —CN,
   g) -methylenedioxy, or pharmaceutically acceptable salts, hydrates and crystal forms thereof, which are useful as antiarrhythmic agents.

The compounds of the present invention may have asymmetric centers and occur as racemates, mixtures of enantiomers, individual diastereomers, or as individual enantiomers with all isomeric forms being included in the present invention. The invention is also concerned with pharmaceutical formulations comprising one of the novel compounds as an active ingredient.

The invention is also concerned with a method of treating arrhythmia by the administration of one or a combination of the novel compounds or formulation thereof to a patient in need of such treatment. These compounds include pharmaceutically acceptable crystal forms and hydrates of the compounds of Formula I, which are antiarrhythmic agents.

One embodiment of the novel compounds of this invention which is synthesized using the process of Scheme I and is shown in Example 1 is N-(2,4-Dioxo-1-phenyl-5-(2-propyl)-2,3,4,5-tetrahydro-1H-1,5-benzodiazepin-3-yl)-3-cyclohexyl propionamide.

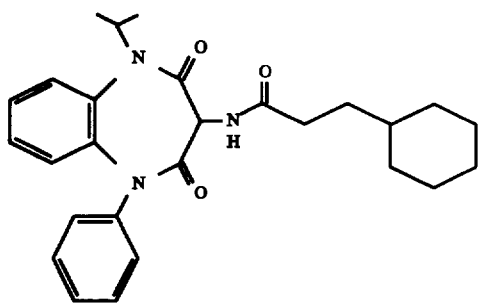

The synthesis of this compound is shown diagramatically in Scheme I and is fully explained in Example 1.

An other embodiment of the novel compounds of this invention is N-(2,4-Dioxo-1-phenyl-5-(2-propyl)-2,3,4,5-tetrahydro-1H-1,5-benzodiazepin-3-yl)-2-(3,5-dichlorophenyl) acetamide.

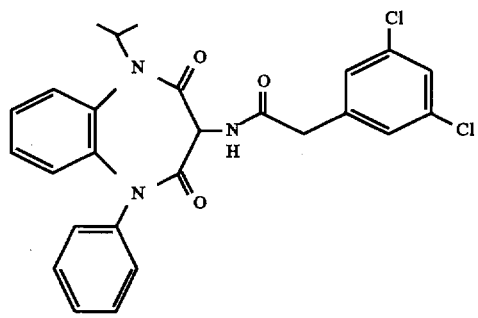

The synthesis of this compound is shown diagramatically in Scheme 1 and is fully explained in Example 2.

An other embodiment of the novel compounds of this invention is N-(2,4-Dioxo-1-phenyl-5-(2-propyl)-2,3,4,5-tetrahydro-1H-1,5-benzodiazepin-3-yl)-3(-2,4-dichlorophenyl) propionamide.

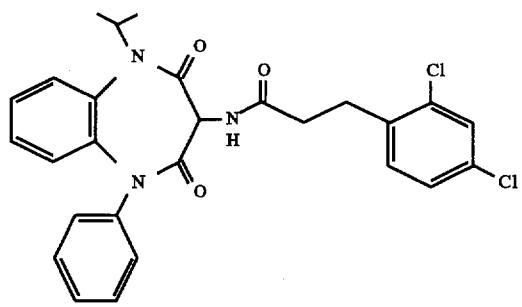

The synthesis of this compound is shwon diagramatically in Scheme 1 and is fully explained in Example 3.

Still an other embodiment of the novel compounds of this invention is N-(2,4-Dioxo-1-phenyl-5-methyl-2,3,4,5-tetrahydro-1H-1,5-benzodiazepin-3yl)-3-(2,4-dichlorophenyl propionamide.

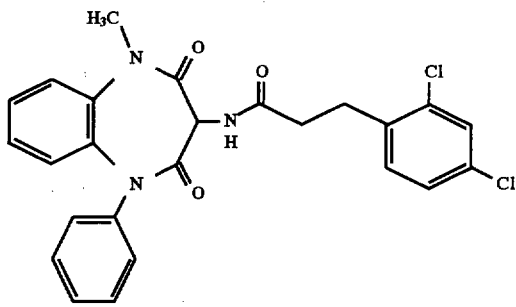

The synthesis of this compound is shown diagramatically in Scheme II, and is fully explained in Example 4.

Still an other embodiment of the novel compounds of this invention is N-(2,4-Dioxo-1-phenyl-5-(2,2,2-trifluoroethyl)-2,3,4,5-tetrahydro-1H-1,5-benzodiazepin-3-yl)-2-(3,5-dichlorophenyl) acetamide.

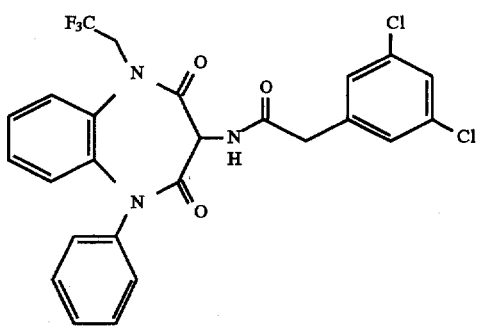

The synthesis of this compound is shwon diagramatically in Scheme III and is fully explained in Example 5.

Still an other embodiment of the novel compounds of this invention is N-(2,4-Dioxo-1-phenyl-5-(2,2,2-trifluoroethyl)-2,3,4,5-tetrahydro-1H-1,5-benzodiazepin-3-yl)-2-(2,4-dichlorophenyl) acetamide.

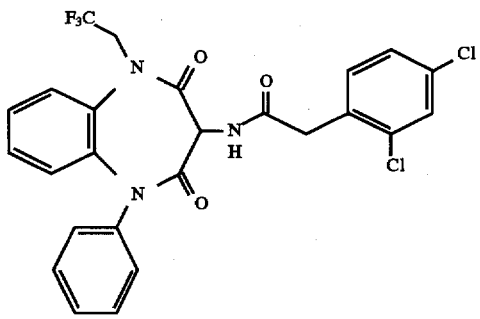

The synthesis of this compound is shown diagramatically in Scheme III and is fully explained in Example 6.

An other embodiment of the novel compounds of this invention is N-(2,4-Dioxo-1-phenyl-5-(2,2,2-trifluoroethyl)-2,3,4,5-tetrahydro-1H-1,5-benzodiazepin-3-yl)-3,4-dichlorobenzamide.

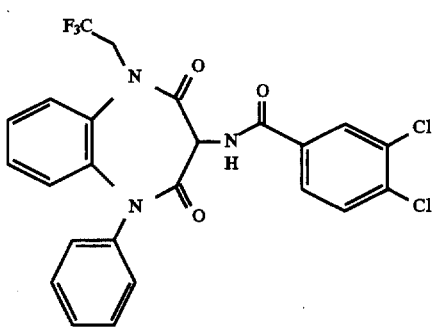

The synthesis of this compound is shown diagramatically in Scheme III and is fully explained in Example 7.

The novel processes for preparing the compounds of this invention are schematically exemplified below in schemes I, II and III. These steps are well known in the art and/or described in the Examples that follow.

Scheme I

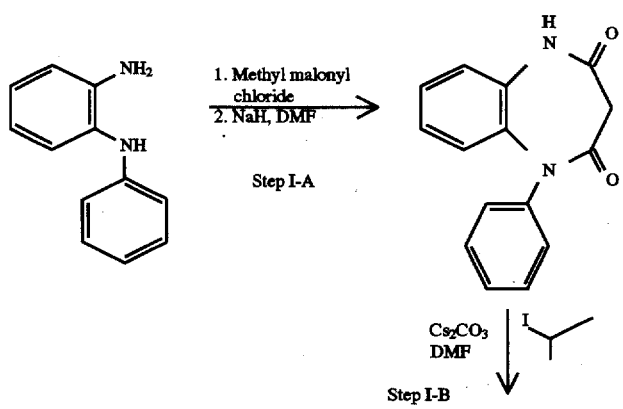

Step I-A

Cs$_2$CO$_3$
DMF

Step I-B

-continued
Scheme I
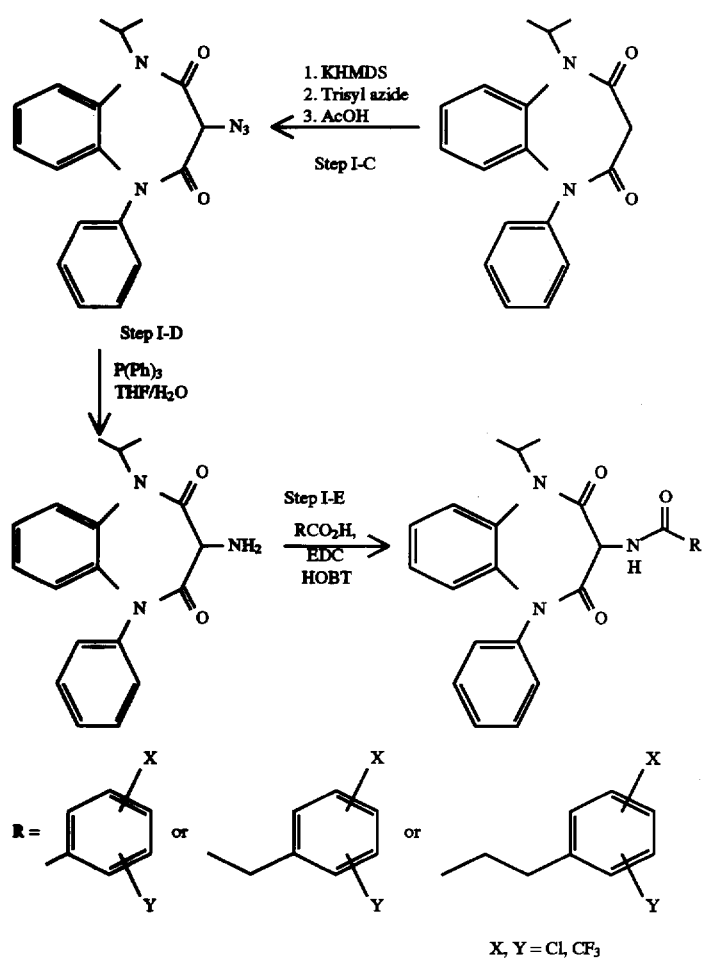
R = (aryl, benzyl, or phenylpropyl substituted with X, Y)
X, Y = Cl, CF$_3$
Scheme II
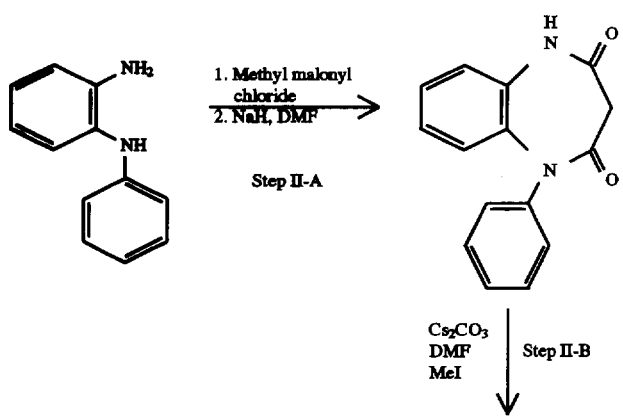

-continued
Scheme II
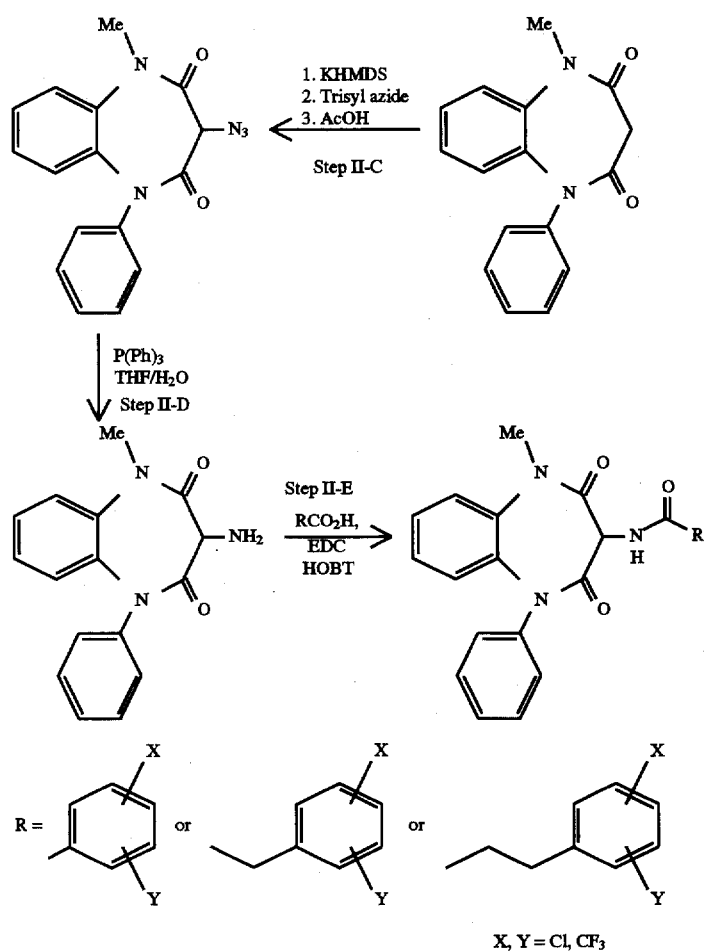
Scheme III
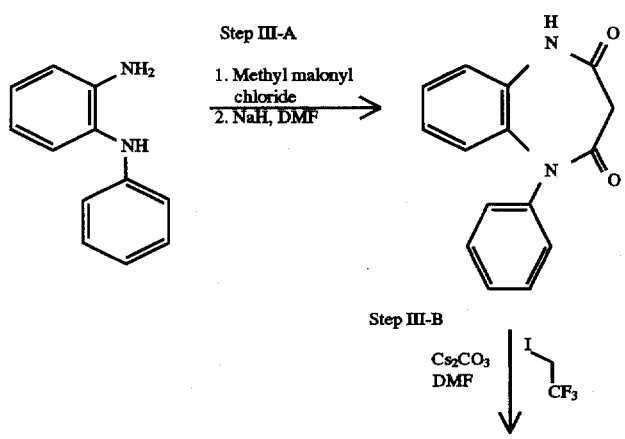

-continued
Scheme III

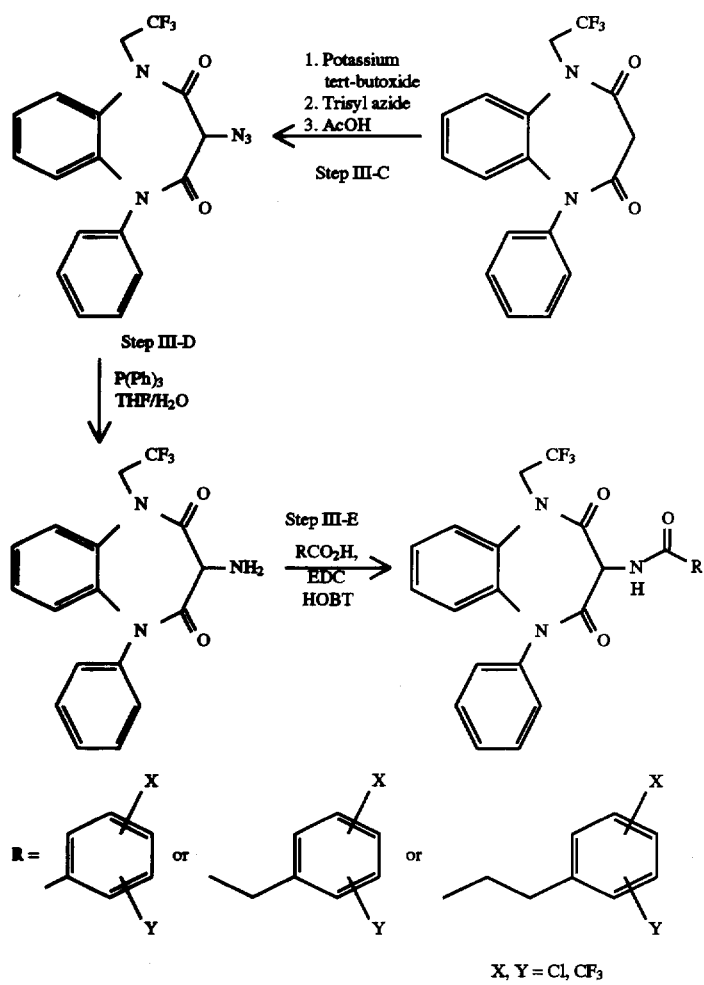

The novel compounds of the present invention, have the pharmacological properties required for antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 5.0 mg per kg of body weight per day in a single dose or in 2 to 4 divided doses.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, emulsions, syrups, wafers, chewing gum, or the like prepared by art recognized procedures. The amount of active compound in such therapeutically useful compositions or preparations is such that a suitable dosage will be obtained.

These compounds can be administered as the sole active ingredient or in combination with other antiarrhythmic agents or other cardiovascular agents, such as Class I, Class II or Class IV antiarrhythmic agents, vasodilators, angiotensin converting enzyme inhibitors, angiotensin II antagonists, diuretics or digitalis.

These compounds can be administered as a method of treating arrhythmia and impaired cardiac pump functions in conjunction with defibrillators, including implantable defibrillators. These compounds reduce the frequency of defibrillator firing.

By Class I antiarrhythmic agents is meant those agents which provide for sodium channel blockade, including those compounds which exert a membrane stabilizing effect. Exemplary of this class of compounds are quinidine, procainamide, disopyramide, lidocane, tocainide, flecainide and propafenone. By Class II antiarrhythmic compounds is meant those agents which block sympathetic activity. Exemplary of this class of compounds are propranolol and acebutolol. By Class III antiarrhythmic agents is meant those compounds which prolong the effective refractory period without altering the resting membrane potential or rate of depolarization. In addition to the novel compounds of this invention, compounds such as amiodarone, bretylium and sotalol are considered to be in this class. Class IV antiarrhythmic agents are effective in calcium channel blockade. Exemplary of this class of compounds are diltiazem and verapamil. Further definition of these classes can be found in Pharma Projects, section C1B, May 1993, which is hereby incorporated by reference.

Exemplary of vasodilators are compounds such as papaverine and isosorbide dinitrat. Examples of angiotensin converting enzyme inhibitors include enalapril, lisinopril and captopril. Examples of diuretics include hydrochlorothiazide and acetazolamide. The pharmaceutical agents listed herein are examples and do not represent a complete listing of the many compounds in these classes which are contemplated by this invention.

The activity of the compounds described herein as antiarrhythmic agents is measured by their ability to block the IKs and IKr currents as determined by the following test protocol.

Outward potassium currents are measured in single guinea pig ventricular myocytes using a whole-cell voltage clamp technique described in detail elsewhere (Sanguinetti and Jurkiewicz, 1990, Two components of cardiac delayed rectifier K$^+$ current: differential sensitivity to block by Class III antiarrhythmic agents. J. Gen Physiol. 96:195–215). Myocytes are isolated by enzymatic (collagenase and protease) digestion of Langandorf perfused hearts. Single cells are then voltage clamped using 1 mm square-bore pipettes filled with 0.5M Kgluconate, 25 mM KCl, 5 mM K(2)ATP. Cells are bathed in a solution containing, in mN: 132 NaCl, 4 KCl, 1.2 MgCl[2], 10 HEPES, 10, glucose: pH 7.2, temp. 35° C.

Each cell is maintained at a holding potential of −50 mV. Test depolarizations are applied as voltage ramps from 31 85 to −50 mV, and as steps to −10 mV (0.5 s) and +50 mV (1.0 s). IKI is measured as peak outward current during the voltage ramp. IKr is measured as tail currents upon repolarization from −10 mV to −50 mV. IKs is measured as time-dependent current during the pulse to +50 mV. Currents are measured during control, then after exposure to drug at two different concentrations.

Employing this test the compounds described herein have an IC$_{50}$ of less than 1,000 nM as IKs blockers. The comounds of this invention are at least 10 times more potent in the blockade of IKs than the blockade of IKr.

EXAMPLES

In the following examples, reference is made to the steps outlined of the schemes found in the Detailed Description of the Invention.

Example 1

N-(2,4-Dioxo-1-phenyl-5-(2-propyl)-2,3,4,5-tetrahydro-1H-1,5-benzodiazepin-3-yl)-3-cyclohexyl propionamide

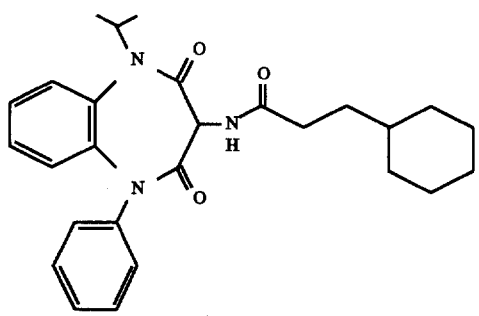

Step I-A: 1-Phenyl-1,5-benzodiazepine-2,4-dione

A solution of N-phenyl-phenylenediamine (10 g, 54.3 mole) in methylene chloride (300 mL) was treated with pyridine (4.73 g, 59.7 mole) and then methyl malonyl chloride (8.15 g, mole). The reaction was stirred at room temperature for 1.5 hours. The mixture was diluted with ethyl acetate (300 mL) and saturated aqueous sodium hydrogen carbonate (500 mL). The organic layer was separated and the aqueous layer was extracted again with ethyl acetate (2×300 mL). The organic layers were combined, dried over anhydrous magnesium sulfate, filtered, and concentrated in vacuo. The residue was dissolved in tetrahydrofuran (500 mL) and sodium hydride (4.87 g of 60% dispersion in mineral oil) was then added and the reaction was stirred at 50° C. for 1.5 hours. The mixture was diluted with ethyl acetate (300 mL) and saturated aqueous sodium hydrogen carbonate (500 mL). The organic layer was separated and the aqueous layer was extracted again with ethyl acetate (2×300 mL). The organic layers were combined, dried over anhydrous magnesium sulfate, filtered, and concentrated in vacuo. The resulting solid was swished with warm ethyl ether (200 mL) and collected by filtration to give 8.5 g (58%) of the product.

$^1$H NMR (300 MHz, CDCl$_3$) δ10.6 (s, 1H), 7.43 (m, 2H), 7.33 (t, J=5 Hz, 1H), 7.2 (m,1H), 7.15 (d, J=6 Hz, 2H), 7.10–7.05 (m, 1H), 6.8 (d, J=6 Hz, 1H)

Step I-B: 1-Phenyl-5-(2-propyl)-1,5-benzodiazepin-2,4-dione

A solution of 1-phenyl-1,5-benzodiazepin-2,4-dione (10 g, 0.040 mole) in N,N-dimethylformamide (80 mL) at room temperature was treated with cesium carbonate (19.4 g, 0.060 mole) and 2-iodopropane (10 g, 0.60 mole), and the reaction was stirred at room temperature for five hours. The reaction was poured into a solution of saturated sodium hydrogen carbonate (600 mL) and extracted with ethyl acetate (3×300 mL). The organic layers were combined, dried over anhydrous magnesium sulfate, filtered, and concentrated in vacuo. The residue was triturated with ether and filtered, giving 7.7 g of white solid. The filtrate was concentrated in vacuo and the residue was chromatographed on silica gel eluting with 1:1 ethyl acetate:hexane to give another 1.7 g of product (80%).

$^1$H NMR (300 MHz, CDCl$_3$) δ7.48–7.11 (m, 8H), 6.93–6.92 (m, 1H), 4.70 (sep, J=7.0 Hz, 1H), 3.50 (d, J=11.4 Hz, 1H), 3.41 (d, J=11.4 Hz, 1H), 1.61 (d, J=7.0 Hz, 3H), 1.34 (d, J=7.0 Hz, 3H).

Step I-C: 3-Azido-1-phenyl-5-(2-propyl)-1,5-benzodiazepin-2,4-dione

To a stirring solution of 1-phenyl-5-(2-propyl)-1,5-benzodiazepin-2,4-dione (500 mg, 0.0017 mole) in tetrahydrofuran (25 mL), which was cooled to −78° C. in a dry ice/acetone bath, was added dropwise potassium bis (trimethylsilyl) amide (0.5M in toluene, 4.1 mL, 0.0020 mole). After ten minutes, 2,4,6-triisopropylbenzenesulfonyl azide (626 mg, 0.0020 mole) in tetrahydrofuran (5 mL) was added dropwise. After ten minutes, acetic acid (0.40 mL, 0.0068 mole) in tetrahydrofuran (5 mL) was added in one portion and the reaction was warmed to room temperature over three hours. The reaction was poured into a solution of saturated sodium hydrogen carbonate (200 mL) and extracted with ethyl acetate (3×100 mL). The organic layers were combined, dried over anhydrous magnesium sulfate, filtered, and concentrated in vacuo. The residue was chromatographed on silica gel eluting with 1:3 ethyl acetate-hexane to give 557 mg of product (98%).

$^1$H NMR (300 MHz, CDCl$_3$) δ7.48–7.18 (m, 8H), 7.03–6.96 (m, 1H), 4.68 (sep, J=7.1 Hz, 1H), 4.18 (s, 1H), 1.63 (d, J=7.0 Hz, 3H), 1.39 (d, J=7.1 Hz, 3H).

Step I-D: 3-Amino-1-phenyl-5-(2-propyl)-1,5-benzodiazepin-2,4-dione

To a stirring solution of 3-azido-1-phenyl-5-(2-propyl)-1,5-benzodiazepin-2,4-dione (500 mg, 0.0015 mole) in tetrahydrofuran (15 mL) and water (3 mL) was added triphenylphosphine (780 mg, 0.0030 mole) and the reaction was stirred at room temperature for 16 hours. The reaction was poured into a 0.1N hydrochloric acid solution (100 mL) and extracted with ether (2×50 mL). The aqueous layer was basified with 12N aqueous sodium hydroxide to pH=10 and extracted with ethyl acetate (3×150 mL). The organic layers were combined, dried over anhydrous magnesium sulfate, filtered, and concentrated in vacuo, yielding a white foam (410 mg, 89%).

$^1$H NMR (300 MHz, CDCl$_3$) δ7.48–7.15 (m, 8H), 6.99–6.92 (m, 1H), 4.68 (sep, J=7.0 Hz, 1H), 4.22 (s, 1H), 1.59 (d, J=7.1 Hz, 3H), 1.36 (d, J=7.0 Hz, 3H).

Step I-E: N-(2,4-Dioxo-1-phenyl-5-(2-propyl)-2,3,4,5-tetrahydro-1H-1,5-benzodiazepin-3-yl)-3-cyclohexyl propionamide To a stirring solution of 3-amino-1-phenyl-5-(2-propyl)-1,5-benzodiazepin-2,4-dione (130 mg, 0.42 mmol) in N,N-dimethylformamide (2 mL) was added EDC (97 mg, 0.50 mmol), HOBT (68 mg, 0.50 mmol) and cyclohexanepropionic acid (79 mg, 0.50 mmol). This was stirred at room temperature for 2 hours. The reaction was diluted with ethyl acetate (150 mL), then washed with 10% aqueous potassium hydrogen sulfate (75 mL) then saturated aqueous sodium hydrogen carbonate (75 mL) and finally, brine (50mL). The organic layer was dried over anhydrous magnesium sulfate, filtered, and concentrated in vacuo. The residue was chromatographed on silica gel eluting with 2:3 ethyl acetate-hexane to give 175 mg of product (93%), which was crystallized from ethyl acetate/hexane to give colorless crystals (130 mg).

m.p.=185°–187° C.

$^1$H NMR (300 MHz, CDCl$_3$) δ7.48–7.17 (m, 8H), 7.03–6.95 (m, 1H), 6.80 (d, J=7.6 Hz, 1H), 5.29 (J=7.6 Hz, 1H), 4.65 (sep, J=7.0 Hz, 1H), 2.40–2.31 (m, 2H), 1.76–1.52 (m, 11H), 1.40–1.05 (m, 6H), 0.97–0.81 (m, 2H).

Anal. Calcd. for C$_{27}$H$_{33}$N$_3$O$_3$: C: 72.46; H: 7.43; N: 9.39. Found: C: 72.55; H: 7.40; N: 9.42.

The following two examples were prepared from 3-amino-1-phenyl-5-(2-propyl)-1,5-benzodiazepin-2,4-dione by a procedure identical to step I-E above except substituting the appropriate carboxylic acid.

Example 2

N-(2,4-dioxo-1-phenyl-5-(2-propyl)-2,3,4,5-tetrahydro-1H-1,5-benzodiazepin-3-yl)-2-(3,5-dichlorophenyl) acetamide

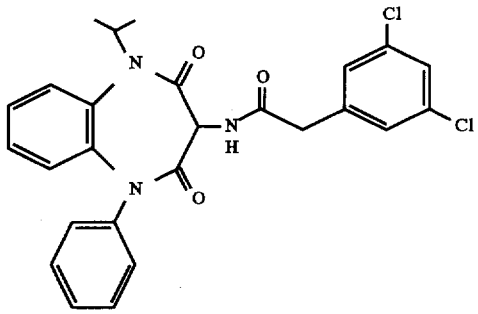

m.p.=181°–182° C.

$^1$H NMR (300 MHz, CDCl$_3$) δ7.50–7.15 (m, 8H), 7.03–6.91 (m, 2H), 5.29 (J=7.6 Hz, 1H), 4.65 (sep, J=7.1 Hz, 1H), 3.63 (s, 2H), 1.58 (d, J=7.1 Hz, 3H), 1.35 (d, J=7.1 Hz, 3H). Anal. Calcd. for C$_{26}$H$_{23}$N$_3$O$_3$Cl$_2$: C: 62.91; H: 4.67; N: 8.47. Found: C: 62.92; H: 4.73; N: 8.43.

Example 3

N-(2,4-Dioxo-1-phenyl-5-(2-propyl)-2,3,4,5-tetrahydro-1H-1,5-benzodiazepin-3-yl)-3-(-2,4-dichlorophenyl) propionamide

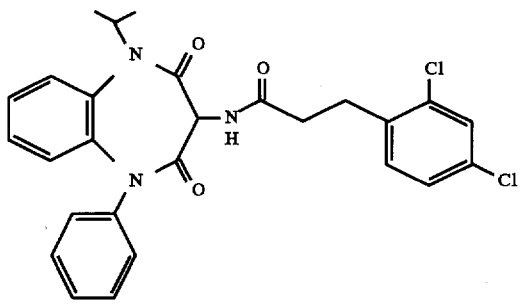

$^1$H NMR (300 MHz, CDCl$_3$) δ7.48–7.13 (m, 8H), 7.03–6.95 (m, 1H), 6.82 (d, J=7.6 Hz, 1H), 5.25 (J=7.6 Hz, 1H), 4.64 (sep, J=7.1 Hz, 1H), 3.06 (t, J=8.0 Hz, 2H), 2.68 (t, J=8.0 Hz, 2H), 1.59 (d, J=7.0 Hz, 3H), 1.36 (d, J=7.0 Hz, 3H).

Anal. Calcd. for C$_{27}$H$_{25}$N$_3$O$_3$Cl$_2$.0.25H$_2$O: C: 62.98; H: 4.99; N: 8.16. Found: C: 62.97; H: 4.91; N: 8.02.

The compound of Example 4 was prepared according to the sequence described in scheme II by procedures substantially as described for the preparation of Examples 1–3 except substituting methyl iodide for 2-iodopropane in step B and then substituting the appropriate carboxylic acid in step II-E.

Example 4

N-(2,4-Dioxo-1-phenyl-5-methyl-2,3,4,5-tetrahydro-1H-1,5-benzodiazepin-3yl)-3-(2,4-dichlorophenyl) propionamide

17

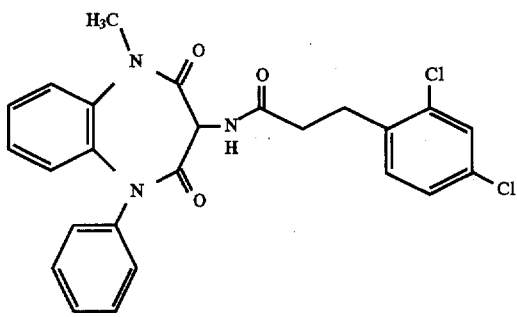

m.p.=196°–198 °C.

¹H NMR (300 MHz, CDCl₃) δ7.48–7.13 (m, 11H), 7.03–6.98 (m, 1H), 6.84 (d, J=7.3 Hz, 1H), 5.29 (J=7.3 Hz, 1H), 3.56 (s, 3H), 3.11 (t, J=7.8 Hz, 2H), 2.69 (t, J=7.8 Hz, 2H). Anal. Calcd. for $C_{25}H_{21}N_3O_3Cl_2$: C: 62.25; H: 4.39; N: 8.71. Found: C: 62.12; H: 4.40; N: 8.59.

The compounds of examples 5, 6 and 7 were prepared according to the route described in scheme III by procedures substantially as described for the preparation of Examples 1–3 from scheme I except substituting trifluoroethyl iodide for 2-iodopropane in step B and then substituting the appropriate carboxylic acid in step III-E.

Example 5

N-(2,4-Dioxo- 1-phenyl-5-(2,2,2-trifluoroethyl)-2,3,4,5-tetrahydro-1H-1,5-benzodiazepin-3-yl)-2-(3,5-dichlorophenyl) acetamide

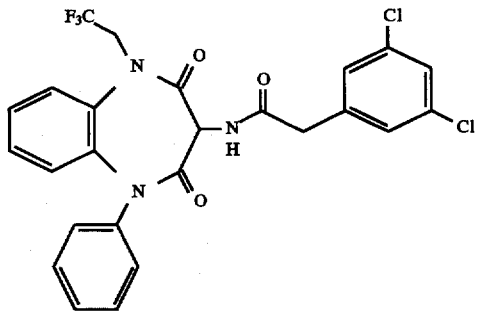

m.p.=209°–210° C.

¹H NMR (300 MHz, CDCl₃) δ7.48–7.18 (m, 11H), 7.06–6.90 (m, 2H), 5.46–5.25 (m, 2H), 4.26–4.10 (m, 1H), 3.62 (s, 2H). Anal. Calcd. for $C_{25}H_{18}N_3O_3Cl_2F_3$: C: 55.99; H: 3.38; N: 7.83. Found: C: 56.00; H: 3.42; N: 7.81.

Example 6

N-(2,4-Dioxo-1-phenyl-5-(2,2,2-trifluoroethyl)-2,3,4,5-tetrahydro-1H-1,5-benzodiazepin-3-yl)-2-(2,4-dichlorophenyl) acetamide

18

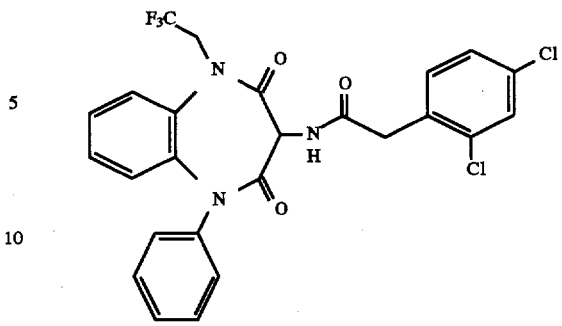

m.p.=211°–212° C.

¹H NMR (300 MHz, CDCl₃) δ7.48–7.15 (m, 11H), 7.06–6.88 (m, 2H), 5.46–5.27 (m, 2H), 4.35–4.09 (m, 1H), 3.80 (s, 2H). Anal. Calcd. for $C_{25}H_{18}N_3O_3Cl_2F_3 \cdot 0.30H_2O$: C: 55.43; H: 3.46; N: 7.76. Found: C: 55.46; H: 3.41; N: 7.79.

Example 7

N-(2,4-Dioxo-1-phenyl-5-(2,2,2-trifluoroethyl)-2,3,4,5-tetrahydro-1H- 1,5-benzodiazepin-3-yl)-3,4-dichlorobenzamide

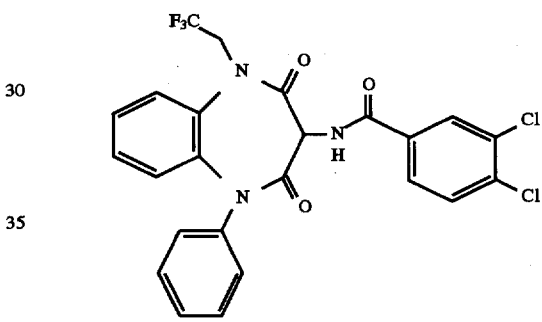

m.p.=219°–220° C.

¹H NMR (300 MHz, CDCl₃) δ8.01–7.21 (m, 11H), 7.07 (s, 1H), 5.54 (d, J=7.9 Hz, 1H), 5.49–5.31 (s, 1H), 4.30–4.12 (m, 1H). Anal. Calcd. for $C_{24}H_{16}N_3O_3Cl_2F_3 \cdot 0.25H_2O$: C: 54.72; H: 3.16; N: 7.98. Found: C: 54.72; H: 3.10; N: 8.06.

What is claimed is:

1. A compound of the structural formula I

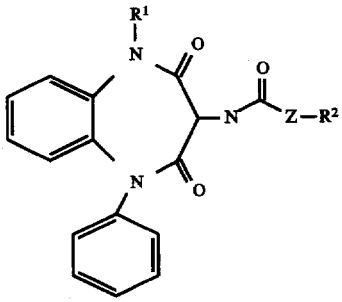

FORMULA I where $R^1$ is $C_{1-6}$ alkyl, either straight or branch chain; substituted $C_{1-6}$ alkyl, either straight or branch chain wherein the substituents are selected from F, $C_{3-8}$ cycloalkane, —OH, —CF₃, and Z is 1) $C_{1-6}$ alkyl, either straight or branched chain, 2) substituted $C_{1-6}$ alkyl, either straight or branched chain, wherein the substituents are selected from F, OH, $NO_2$,
2) $C_{2-4}$ alkenylene, either straight or branched chain,
3) $C_{3-6}$ cycloalkane,
4) $C_{3-6}$ cycloalkylene, or
5) single bond;

$R^2$ is
1) $C_{5-7}$ cycloalkyl, either unsubstituted or substituted with one or two substituents selected from
   a) $-NO_2$, $-OH$,
   b) $-F$,
   c) $-CF_3$,
   d) $-C_{1-3}$ alkyl,
   e) $-C_{1-3}$ alkoxy,
   f) $-CN$,
   g) -methylenedioxy, as the racemates, mixtures of enantiomers, individual diastereomers or individual enantiomers, and pharmaceutically acceptable crystal forms, salts, or hydrates thereof.

2. The compound of claim 1 which is N-(2,4-Dioxo-1-phenyl-5-(2-propyl)-2,3,4,5-tetrahydro-1H-1,5-benzodiazepin-3-yl)-3-cyclohexyl propionamide

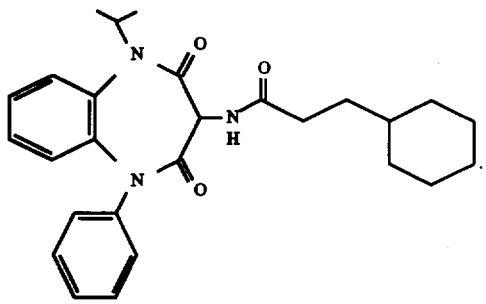

3. A pharmaceutical formulation comprising a pharmaceutically acceptable carrier and a therapeutically effective amount of the compound of claim 1 or a pharmaceutically acceptable salt, crystal form or hydrate thereof.

4. The compound of claim 1 which is N-(2,4-Dioxo-1-phenyl-5-(2-propyl)-2,3,4,5-tetrahydro-1H-1,5-benzodiazepin-3-yl)-3-cyclohexyl propionamide;

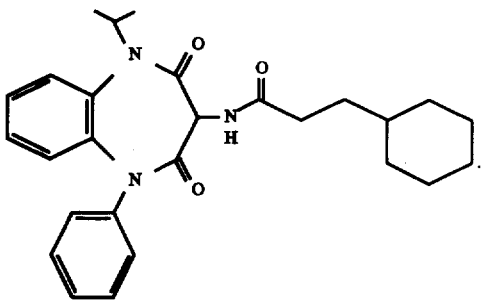

5. A method of preventing or treating arrhythmia which comprises the administration to a patient in need of such treatment of an antiarrhythmically effective amount of a compound of structural formula I

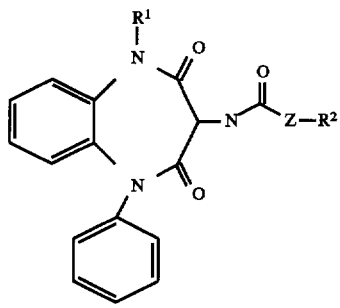

FORMULA I where $R^1$ is $C_{1-6}$ alkyl, either straight or branch chain; substituted $C_{1-6}$alkyl, either straight or branch chain wherein the substituents are selected from F, $C_{3-8}$ cycloalkane, $-OH$, $-CF_3$, and Z is
1) $C_{1-6}$ alkyl, either straight or branched chain,
2) substituted $C_{1-6}$ alkyl, either straight or branched chain, wherein the substituents are selected from F, OH, $NO_2$,
3) $C_{2-4}$ alkenylene, either straight or branched chain,
4) $C_{3-6}$ cycloalkane,
5) $C_{3-6}$ cycloalkylene, or
6) single bond;

$R^2$ is
1) phenyl, either unsubstituted or substituted with one or two substituents selected from
   a) $-NO_2$, $-OH$,
   b) $-Cl$, Br, F, or I,
   c) $-CF_3$,
   d) $-C_{1-3}$ alkyl,
   e) $-C_{1-3}$ alkoxy,
   f) $-CN$,
   g) -methylenedioxy,
2) $C_{5-7}$ cycloalkyl, either unsubstituted or substituted with one or two substituents selected from
   a) $-NO_2$, $-OH$,
   b) $-F$,
   c) $-CF_3$,
   d) $-C_{1-3}$ alkyl,
   e) $-C_{1-3}$ alkoxy,
   f) $-CN$,
   g)-methylenedioxy, as the racemates, mixtures of enantiomers, individual diastereomers or individual enantiomers, and pharmaceutically acceptable crystal forms, salts, or hydrates thereof.

* * * * *